(12) United States Patent
von Samson-Himmelstjerna et al.

(10) Patent No.: US 11,294,013 B2
(45) Date of Patent: Apr. 5, 2022

(54) IMAGING SYSTEM FOR GENERATING A SERIES OF IMAGES

(71) Applicant: Fraunhofer-Gesellschaft zur Foerderung der angewandten Forschung e.V., Munich (DE)

(72) Inventors: Federico von Samson-Himmelstjerna, Munich (DE); Nora-Josefin Breutigam, Bremen (DE); Matthias Guenther, Bremen (DE)

(73) Assignee: Fraunhofer-Gesellschaft zur Förderung der angewandten Forschung e.V., Munich (DE)

(*) Notice: Subject to any disclaimer, the term of this patent is extended or adjusted under 35 U.S.C. 154(b) by 648 days.

(21) Appl. No.: 16/095,347

(22) PCT Filed: Apr. 20, 2017

(86) PCT No.: PCT/EP2017/059409
§ 371 (c)(1),
(2) Date: Oct. 19, 2018

(87) PCT Pub. No.: WO2017/182575
PCT Pub. Date: Oct. 26, 2017

(65) Prior Publication Data
US 2019/0128988 A1  May 2, 2019

(30) Foreign Application Priority Data

Apr. 20, 2016 (DE) .................. 102016206724.9

(51) Int. Cl.
*G01R 33/563* (2006.01)
*G01R 33/483* (2006.01)
*A61B 5/055* (2006.01)

(52) U.S. Cl.
CPC ........ *G01R 33/56366* (2013.01); *A61B 5/055* (2013.01); *G01R 33/4833* (2013.01); *G01R 33/4838* (2013.01)

(58) Field of Classification Search
None
See application file for complete search history.

(56) References Cited

U.S. PATENT DOCUMENTS

| | | |
|---|---|---|
| 2014/0081123 A1 | 3/2014 | Korosec et al. |
| 2014/0347048 A1 | 11/2014 | Sun et al. |
| 2018/0180697 A1* | 6/2018 | Samson-Himmelstjerna ............. A61B 5/0263 |

FOREIGN PATENT DOCUMENTS

| | | |
|---|---|---|
| CN | 101254101 | 9/2008 |
| CN | 104919330 | 9/2015 |

(Continued)

OTHER PUBLICATIONS

Breutigam, "Automatic adaption of Arterial Spin Labeling parameters: Walsh-sorted time-encoded pCASL with dynamic feedback", Masters Thesis., Mar. 2016. (Year: 2016).*

(Continued)

*Primary Examiner* — Katherine L Fernandez
(74) *Attorney, Agent, or Firm* — Lowe Graham Jones LLC; Ellen M. Bierman

(57) ABSTRACT

The invention relates to an imaging system for generating a series of images of a subject. Fluid boli are generated at a first location of the subject, wherein each fluid bolus comprises a sequence of sub-boli and wherein images of the series of images are acquired at a second location of the subject, after the fluid boli have been flowed to the second location. A sub-bolus length is determined based on at least one image of the already acquired images of the series of images, wherein a further fluid bolus comprising a sequence of sub-boli is generated at the first location, wherein at least (Continued)

one of the sub-boli has the determined sub-bolus length, and wherein a further image of the series of images is acquired at the second location of the subject, after the further fluid bolus has been flowed from the first location to the second location.

17 Claims, 6 Drawing Sheets

(56) References Cited

FOREIGN PATENT DOCUMENTS

| CN | 105488804 | | 4/2016 |
|---|---|---|---|
| DE | 10 2014 205 789 | | 10/2015 |
| WO | WO 2015/144768 | * | 10/2015 |

OTHER PUBLICATIONS

Breutigam et al., "Automatic adaption of ASL labeling parameters: Walsh-sorted time-encoded pCASL with a dynamic feedback algorithm," Proceedings of the International Society for Magnetic Resonance in Medicine, ISMRM, 24th Annual Meeting and Exhibition, Singapore, May 7-13, 2016, No. 1000, Apr. 22, 2016, XP040682043, Sections "Purpose", "Theory", 3 pages.

Dai et al., "Continuous Flow-Driven Inversion for Arterial Spin Labeling Using Pulsed Radio Frequency and Gradient Fields," Magnetic Resonance in Medicine 60:1488-1497 (2008).

Dai et al., "Reduced resolution transit delay prescan for quantitative continuous arterial spin labeling perfusion maging", Magnetic Resonance in Medicine, vol. 67, No. 5, May 1, 2012, pp. 1252-1265, XP55027263, ISSN 0740-3194, DOI: 10.1002/mrm.23103, Sections "Theory", "Materials and Methods".

Dai et al., "Volumetric measurement of perfusion and arterial transit delay using hadamard encoded continuous arterial spin labeling : Hadamard Encoded Arterial Spin Labeling", Magnetic Resonance in Medicine, vol. 69, No. 4, Apr. 1, 2013, pp. 1014-1022, XP055405404, ISSN: 0740-3194, DOI: 10.1002/mrm.24335 cited in the application Sections "Theory", "Methods".

Detre, "Perfusion Imaging", Magnetic Resonance in Medicine 23, 37-45 (1992).

International Search Report and Written Opinion of the International Searching Authority completed Sep. 12, 2017, in International Patent Application No. PCT/EP2017/059409, 13 pages.

Teeuwisse et al., "Time-encoded pseudocontinuous arterial spin labeling: Basic properties and timing strategies for human applications", Magnetic Resonance in Medicine, vol. 72, No. 6, Jan. 6, 2014, pp. 1712-1722, XP55193384, ISSN: 0740-3194, DOI: 10.1002/mrm.25083.

Von Samson-Himmelstjerna et al., "Walsh-ordered hadamard time-encoded pseudocontinuous ASL (WH pCASL) : Walsh-Ordered Hadamard Time-Encoded pCASL", Magnetic Resonance in Medicine, vol. 76, No. 6, Dec. 30, 2015, pp. 1814-1824, XP055406038, ISSN: 0740-3194, DOI: 10.1002/mrm.26078.

Wang et al., "Multi-delay multi-parametric arterial spin-labeled perfusion MRI in acute ischemic stroke—Comparison with dynamic susceptibility contrast enhanced perfusion imaging," NeuroImage: Clinical 3 (2013) 1-7.

Wells et al., "In vivo hadamard encoded continuous arterial spin labeling (H-CASL)", Magnetic Resonance in Medicine, vol. 63, No. 4, Apr. 1, 2010, pp. 1111-1118, XP55143323, ISSN: 0740-3194, DOI: 10.1002/mrm.22266.

* cited by examiner

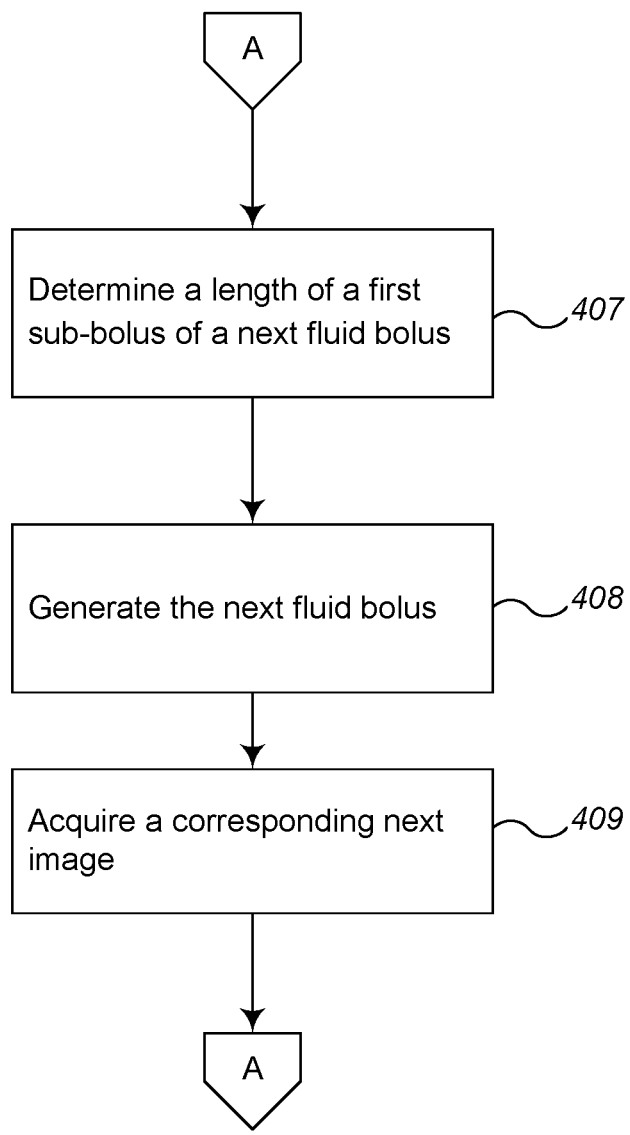
Fig. 5 (Con't)

IMAGING SYSTEM FOR GENERATING A SERIES OF IMAGES

CROSS-REFERENCE TO RELATED APPLICATIONS

This application is a U.S. national phase of International Patent Application No. PCT/EP2017/059409 filed Apr. 20, 2017, which claims priority from Germany Patent Application No. 10 2016 206 724.9 filed Apr. 20, 2016, the contents of which applications are incorporated herein by reference in their entireties.

TECHNICAL FIELD

The invention relates to an imaging system, an imaging method and a computer program for generating a series of images of a subject.

BACKGROUND

In clinical diagnostics or in biomedical research the determination of hemodynamic parameters like blood volume, permeability, and blood flow (perfusion) is of great relevance to acquire information about the status and functionality of tissue and organs. For many applications one of the most important parameters is the perfusion of the blood in a tissue of interest.

In medical imaging different methods are used to determine this parameter. For instance, for measuring the blood flow within a tissue of interest a contrast agent can be injected into the blood system of a patient and several images of the tissue of interest can be acquired at different points in time. From the acquired images showing the distribution of the contrast agent in the tissue at different time points the perfusion, dynamics and kinetics of the blood can be determined.

Instead of injecting a contrast agent, like for instance Gadolinium, non-invasive contrast techniques can be used, in which an endogenous contrast agent like the blood of the patient is utilized. One of these non-invasive techniques that allow for a time resolved measurement of the blood flow in a tissue of interest is arterial spin labeling (ASL).

In ASL a part of the blood is labeled at a certain location, for instance, at the neck of the patient and, after a certain waiting time in which the labeled blood can travel from the labeling site to the tissue of interest, a medical image of the tissue of interest is acquired using preferably an MR system. By using this non-invasive ASL technique for determining the perfusion of the blood in the tissue, the results are strongly dependent on the arterial transit time (ATT) of the blood, i.e. the time that is necessary for the blood to reach the capillary bed of the tissue of interest. This ATT can show a high variability especially in cases of abnormal variations in the tissue of interest, which can lead to the so-called arterial transit delay (ATD) artifact, wherein an ATD artifact occurs, when an MR signal from the tissue of interest, i.e. an MR signal from the labeled blood within the tissue of interest, is generated in some voxels by labeled blood having already reached the capillary bed and in some by labeled blood which is still present in the arteries and has not reached the capillary bed.

In an example in which the brain is the tissue of interest typical anomalies that lead to a delayed inflow of labeled blood into the capillary bed are, for instance, stenoses, Alzheimer's disease or Moyamoya disease. If in these cases the time between the labeling of the blood and the acquisition of the medical image, the so-called post-labeling delay or inflow time, is not chosen accordingly to enable the blood to be completely expanded into the capillary bed of the tissue of interest, during perfusion measurements strong ATD artifacts may occur. Since the ATT and therefore the post-labeling delay can strongly depend on the individual patient, it is not possible to give a general recommendation to the clinician for choosing the post-labeling delay.

Different ASL techniques for measuring the perfusion and inflow of blood into a tissue of interest are known. To measure the inflow time (TI) dependent signal change different methods are known. These include for instance the straightforward multi-TI technique, where different TI are acquired sequentially after individual labeling preparations. A well-known speed-up are Look-Locker approaches with multiple different TI being acquired after one labeling preparation. Known look-locker or multi TI-methods can be used to determine the temporal development of the blood signal, i.e. a time-resolved inflow and perfusion of the blood in the tissue of interest can be determined. However, this technique can only be combined with gradient-echo based readout approaches. Furthermore, it is for instance known to use a Hadamard time encoded pseudo continuous ASL (te-pCASL) technique, which is also described, for instance, in the articles "Highly efficient accelerated acquisition of perfusion inflow series by Cycled Arterial Spin Labeling" by M. Guenther, Proceeding of the 15th Annual Meeting of ISMRM, volume 15, page 380 (2007), "Volumetric measurement of Perfusion and Arterial Transit Delay using Hadamard Encoded Continuous Arterial Spin Labeling" by W. Dai et al., Magnetic Resonance in Medicine, volume 69, pages 1014 to 1022 (2012) and "Time-Encoded pseudoContinuous Arterial Spin Labeling: Basic Properties and Timing Strategies for Human Applications" by W. M. Teeuwisse et al., Magnetic Resonance in Medicine, volume 72, pages 1712 to 1722 (2014), which are herewith incorporated by reference, wherein the blood is divided into blood boli having labeled or non-labeled parts, i.e. sub-boli, that are generated by applying the labeling or non-labeling over a certain time at one location such that discrete amounts of blood are formed within the blood vessels. Due to the blood flow these extend over a certain length within the blood vessel. The te-pCASL technique can be used for acquiring different images for several differently encoded blood boli, which can also be called coded blood boli, wherein a respective medical image is acquired a certain time after a respective blood bolus, which is composed of individual sub-boli, has been generated, in order to allow the respective blood bolus to reach the tissue of interest.

Known methods can then be used for decoding the information in the images resulting from each individual sub-bolus. Since for each sub-bolus the time between the end of the generation of the sub-bolus and the time of the acquisition of the image is known this yields a temporal sampling of the signal.

In the te-pCASL technique the blood boli are encoded according to a Hadamard matrix. In this case each row of the Hadamard matrix determines a sequence of labeled and non-labeled states of the sub-boli forming a respective blood bolus. Thus, each row of the Hadamard matrix is indicative of a blood bolus, wherein all rows of the Hadamard matrix indicate a series of blood boli, wherein for each blood bolus an image is acquired being indicative of the respective blood bolus. Using an N×N matrix N images, that are indicative of the N net blood boli of the matrix, have to be acquired in order to encode N−1 time-resolved images showing the blood flowing into the tissue of interest. By decoding the images using known methods as described, for instance, in the above mentioned articles "Highly efficient accelerated acquisition of perfusion inflow series by Cycled Arterial Spin Labeling" by M. Guenther, "Volumetric measurement of Perfusion and Arterial Transit Delay using Hadamard Encoded Continuous Arterial Spin Labeling" by W. Dai et al. and "Time-Encoded pseudoContinuous Arterial Spin Labeling: Basic Properties and Timing Strategies for Human Applications" by W. M. Teeuwisse et al., in the article "Walsh-Ordered Hadamard Time-Encoded Pseudocontinuous ASL (WH pCASL)", by F. von Samson-Himmelstjerna et al., Magnetic Resonance in Medicine (2015) and in the U.S. Pat. No. 8,260,396, which are herewith incorporated by reference, this technique allows for a time-resolved measurement of the inflow of the blood into the tissue of interest.

Commonly, single-TI methods are used for the image read-out. However, also known look-locker or multi TI-methods can be used instead to determine the temporal development of the blood signal in even finer steps, i.e. inflow and perfusion of the blood in the tissue of interest can be determined with high temporal resolution.

If in addition to the time-resolved images for sampling the inflow and perfusion of the blood also static perfusion images or other parameters are to be determined, the first sub-bolus of each blood bolus measured during the te-pCASL technique may be used to acquire a static perfusion image of the tissue of interest. Thus, with one measurement both the time dependency of the inflowing blood and also the static perfusion signal of the blood being totally incorporated into the capillary bed of the tissue of interest can be determined. Therefore, this technique is known as the free lunch technique (te-pCASLFL). An important aspect is, that for determining the time dependency of the inflowing blood and the perfusion signal of the blood being totally incorporated into the capillary bed of the tissue of interest neither the time for the measurements has to be prolonged nor the signal-to-noise ratio (SNR) is decreased.

The free lunch technique can be combined with the so-called Walsh-ordered Hadamard time-encoded pseudo-continuous ASL (WH-pCASL) technique disclosed for instance in "Walsh-Ordered Hadamard Time-Encoded Pseudocontinuous ASL (WH pCASL)", by F. von Samson-Himmelstjerna et al., wherein this technique allows determining information about the time dependency of the inflow of the blood in the tissue of interest before all N images of a series of images, which correspond to a series of blood boli that are encoded by using a Walsh-ordered Hadamard matrix, are acquired completely. By evaluating information, which has been determined based on already acquired images, disturbances and errors, e.g. due to motion, can be identified during an early phase of the image acquisition such that the acquisition of the series of images can be interrupted or, if the disturbances or error are too strong, repeated.

The temporal length of the blood boli, the temporal length of the sub-boli of the blood boli, the temporal distance between the generation of the respective blood bolus and the acquisition of the respective image and hence the post-labeling delay times are predetermined and generally the same for each patient. This timing information and also other parameters are therefore not adapted to the respective patient such that the above mentioned ATD artifacts occur, thereby reducing the quality of the acquired images.

SUMMARY

It is an object of the present invention to provide an imaging system, an imaging method and a computer program for acquiring a series of images of a subject, which have less image artifacts.

In a first aspect of the present invention an imaging system for generating a series of images of a subject is presented, wherein the imaging system comprises:
 a bolus generating unit for generating fluid boli at a first location of the subject, wherein each fluid bolus comprises a sequence of sub-boli, wherein each sub-bolus has one of at least two different labeling states,
 an image acquisition unit for acquiring images of the series of images at a second location of the subject at a respective acquisition time, after the fluid boli have been flowed from the first location to the second location, wherein each image corresponds to a respective fluid bolus, and
 a sub-bolus length determination unit for determining a sub-bolus length based on at least one image of the acquired images of the series of images
 wherein the bolus generating unit is adapted to generate a further fluid bolus comprising a sequence of sub-boli at the first location, wherein at least one of the sub-boli has the determined sub-bolus length, and
 wherein the image acquisition unit is adapted to acquire a further image of the series of images at the second location of the subject, after the further fluid bolus has been flowed from the first location to the second location.

DETAILED DESCRIPTION

Figure 1:
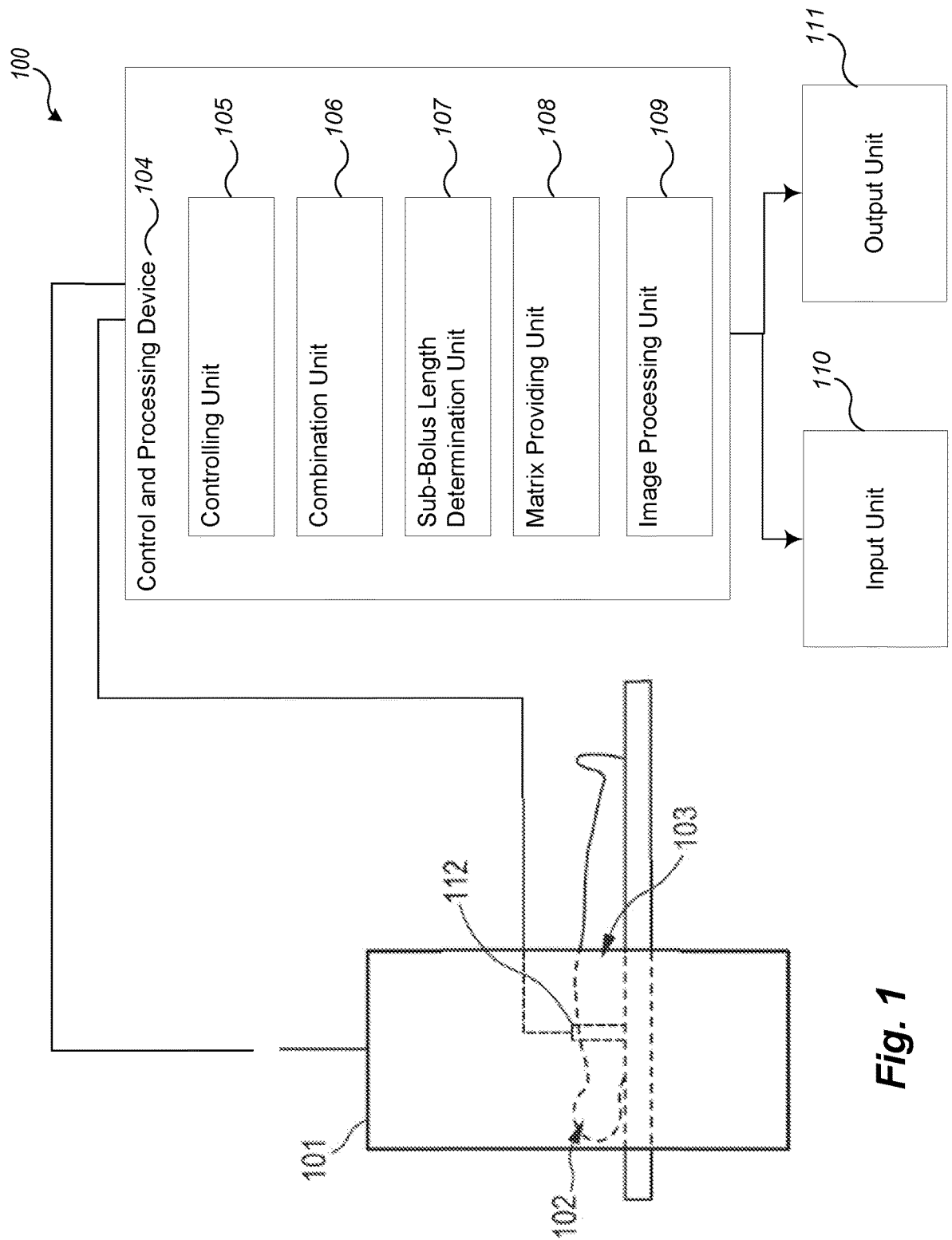
FIG. 1 shows schematically and exemplarily an embodiment of an imaging system for generating a series of images.

In a first aspect of the present invention an imaging system for generating a series of images of a subject is presented, wherein the imaging system comprises:
 a bolus generating unit for generating fluid boli at a first location of the subject, wherein each fluid bolus comprises a sequence of sub-boli, wherein each sub-bolus has one of at least two different labeling states,
 an image acquisition unit for acquiring images of the series of images at a second location of the subject at a respective acquisition time, after the fluid boli have been flowed from the first location to the second location, wherein each image corresponds to a respective fluid bolus, and
 a sub-bolus length determination unit for determining a sub-bolus length based on at least one image of the acquired images of the series of images
 wherein the bolus generating unit is adapted to generate a further fluid bolus comprising a sequence of sub-boli at the first location, wherein at least one of the sub-boli has the determined sub-bolus length, and
 wherein the image acquisition unit is adapted to acquire a further image of the series of images at the second location of the subject, after the further fluid bolus has been flowed from the first location to the second location.

Since the sub-bolus length determination unit determines a sub-bolus length based on at least one image of the acquired images of the series of images which has been acquired already, the combination image and hence the determined sub-bolus length are subject specific. Moreover, since the generation of the further fluid bolus and a corresponding further image considers this subject specific sub-bolus length, the timing of the generation of the further fluid bolus comprising the sub-bolus having the determined length can be subject specific, which allows for a subject specific timing of the measurement process and hence for an improved image quality. Thus, after only a part of the series of images has been acquired already, at least one of the images being an image of the already acquired part of the series of images is used to determine the subject specific length such that a remaining part of the series of images can be acquired using the determined subject specific length. The acquisition of the series of images can therefore be adapted to the specific subject during the acquisition of the series of images.

The different labeling states of the sub-boli can refer to different physical or chemical states of the fluid. At least one of the labeling states is visible in an image acquired by the image acquisition unit. In one embodiment the different labeling states refer to a labeling state and a non-labeling state of the fluid, wherein in the labeling state the physical or chemical state of the fluid is changed compared with the natural state of the fluid and in the non-labeling state the fluid is in its natural state. The sub-bolus length determination unit can be adapted to determine a temporal length and/or a spatial length of a sub-bolus, wherein the temporal length and the spatial length of a sub-bolus are connected via the flow velocity of the fluid.

The fluid is preferentially blood. However, the fluid can also be another fluid like cerebro spinal fluid or a contrast agent. Preferentially, the fluid boli have a same temporal length, wherein the difference between the time of generating a respective fluid bolus and the acquisition time for acquiring the respective image is the same for all combinations of the respective image and a corresponding respective fluid bolus.

Preferentially, the imaging system further comprises a combination unit for generating a combination image by combining at least two of the acquired images, wherein the combination image is indicative of a combination fluid bolus being indicative of a combination of at least two fluid boli, wherein the sub-bolus length determination unit determines the sub-bolus length based on the generated combination image.

The combination image refers to an image that would result from combining a) an image that would correspond to a respective applied combination bolus and b) a control image that would correspond to a control fluid bolus, wherein the control fluid bolus has only one labeling state. Thus, the combination image is indicative of the combination bolus. In an embodiment the labeling states refer to a labeled state and a non-labeled state of the fluid, wherein the combination bolus refers to a fluid bolus comprising at least one labeled sub-bolus and the control fluid bolus refers to a fluid bolus being non-labeled. In this case the combination image can be regarded as an image acquired using a standard multi TI- or multi PLD-method and the combination bolus refers to a fluid bolus applied, i.e. generated, during the standard multi TI-method. The well known standard multi TI- and multi PLD-methods are disclosed, for instance, in the articles "Multiple inflow pulsed arterial spin-labeling reveals delays in the arterial arrival time in minor stroke and transient ischemic attack" by B. MacIntosh and 'Multi-delay multi-parametric arterial spin-labeled perfusion MRI in acute ischemic stroke—Comparison with dynamic susceptibility contrast enhanced perfusion imaging' by D. Wang et al., which are herewith incorporated by reference.

Preferentially, the bolus generating unit is adapted to generate the further fluid bolus such that the first sub-bolus of this further fluid bolus has the determined sub-bolus length, i.e. preferentially the sub-bolus length determination unit determines the length of the first sub-bolus of the further fluid bolus. The first sub-bolus is the sub-bolus among the sub-boli forming the further fluid bolus, which is generated first.

Preferentially, the further image of the series of images is the image, which immediately follows the already acquired images of the series of images. Correspondingly, the further fluid bolus immediately follows the fluid boli to which the already acquired images correspond.

The combination unit can be adapted to determine one or several combination images. Correspondingly, the sub-bolus length determination unit can be adapted to determine a sub-bolus length based on one or several generated combination images.

In an embodiment the fluid boli have a same temporal length, wherein the difference between the time of generating a respective fluid bolus and the acquisition time for acquiring the respective image is the same for all combinations of the respective image and a corresponding respective fluid bolus, wherein each sub-bolus has a first end and a second end, wherein the first end is generated earlier then the second end, wherein the image acquisition unit is adapted to acquire the series of images at the second location such that it shows a capillary bed, wherein the sub-bolus length determination unit, the bolus generation unit and the image acquisition unit are adapted such that the time period between a) the time, at which the second end of the first sub-bolus of the further fluid bolus is generated at the first location, and b) the time, at which the further image which corresponds to the further fluid bolus is acquired at the second location, is equal to or larger than the time needed by the second end of the first sub-bolus to be flowed from the first location to the second location and into the capillary bed. In particular each fluid bolus has first and second ends, wherein the first end is generated earlier then the second end, wherein the bolus generation unit and the image acquisition unit are adapted such that the time period between a) the time, at which the second end of the further fluid bolus is generated at the first location and the acquisition time of the further image at the second location is predetermined, wherein the bolus generating unit is adapted to determine the further fluid bolus such that the length of the further fluid bolus is predetermined, wherein the sub-bolus length determination unit is adapted to determine the sub-bolus length of the first sub-bolus of the further fluid bolus such that the time period between a) the time, at which the second end of the first sub-bolus is generated, and b) the time, at which the further image which corresponds to the further fluid bolus comprising the first sub-bolus is acquired, is equal to or larger than the time needed by the second end of the first sub-bolus to be flowed from the first location to the second location and into the capillary bed.

The post-labeling delay time for a sub-bolus is preferentially defined as the time between the end of the generation of the sub-bolus, i.e. the second end, and the acquisition time of the image which corresponds to the fluid bolus that includes the sub-bolus. Since each fluid bolus has the same length and for each combination of an acquired image and a respective corresponding fluid bolus the time period between a) the end of the generation of the respective fluid bolus and b) the acquisition time of the respective image are the same, the post-labeling delay time and the determined length of the sub-bolus depend on each other. By modifying the length of a sub-bolus the post-labeling delay time for the sub-bolus can therefore be modified. Shortening the sub-bolus length leads to a longer post-labeling delay time for the sub-bolus and prolonging a sub-bolus leads to a shorter post-labeling delay time for the sub-bolus. The modification of the length of the sub-bolus allows therefore for a modification of the post-labeling delay time during the process of acquiring the series of images. Information from already acquired images can hence be used for optimizing the post-labeling delay time for sub-boli to be used for acquiring further images of the series of images.

In an embodiment the sub-bolus length is determined such that the post-labeling delay time of the first sub-bolus in a sequence of sub-boli forming the further fluid bolus lies at the end of a transition time between an arterial capillary transitional phase and a pure capillary phase of a region of interest. In the arterial capillary transitional phase only a part of the labeled fluid has entered the capillary bed of the region of interest, wherein in the pure capillary phase all of the labeled fluid has entered the capillary bed of the region of interest, even in those areas having the longest fluid inflow time within a region of interest. Choosing the subject specific length of the first sub-bolus in the further fluid bolus such that the post-labeling delay time for the first sub-bolus lies at the end of the transition time between the arterial capillary transitional phase and the pure capillary phase of the region of interest can lead to an avoidance of the occurrence of ATD artifacts caused by labeled fluid that is still found in the arteries.

In an embodiment the fluid boli have a same temporal length, wherein the difference between the time of generating a respective fluid bolus and the acquisition time for acquiring the respective image is the same for all combinations of the respective image and a corresponding respective fluid bolus, wherein the respective temporal length of the respective fluid bolus is defined relative to the respective acquisition time, wherein a first end of the respective temporal length has a larger distance to the respective acquisition time than a second end of the respective temporal length, wherein this relative temporal length is the same for different fluid boli and for combination boli being the combination of several fluid boli. In an embodiment the combination unit is adapted to generate a first combination image by combining at least two of the acquired images such that it is indicative of a first combination bolus including only a single combination sub-bolus, which has a first labeling state, and to generate a second combination image by combining at least two of the acquired images such that it is indicative of a second combination bolus including only a single combination sub-bolus, which has the first labeling state, wherein each of the single combination sub-boli, which have the first labeling state, has first and second ends, wherein the first end of the single combination sub-bolus, which has the first labeling state, of the first combination bolus is closer to the first end of the first combination bolus than the second end of the single combination sub-bolus, which has the first labeling state, wherein the first end of the single combination sub-bolus, which has the first labeling state, of the second combination bolus is closer to the first end of the second combination bolus than the second end of this single combination sub-bolus, which has the first labeling state, wherein:

i) a first temporal distance between a) the second end of the single combination sub-bolus, which has the first labeling state, of the first combination bolus and b) the second end of the first combination bolus is larger than a second temporal distance between a) the second end of the single combination sub-bolus, which has the first labeling state, of the second combination bolus and b) the second end of the second combination bolus, and/or ii) a third temporal distance between a) the first end of the single combination sub-bolus, which has the first labeling state, of the first combination bolus and b) the second end of the first combination bolus is larger than a fourth temporal distance between a) the first end of the single combination sub-bolus, which has the first labeling state, of the second combination bolus and b) the second end of the second combination bolus, wherein the sub-bolus length determination unit is adapted to determine the sub-bolus length of the fluid bolus, to which the further image corresponds, based on the first and second combination images. In this case the combination images are combined from the series of images such that the combination images are indicative of a fluid bolus comprising only one labeled combination sub-bolus.

The combination images can be regarded as images that would result from a combination of a) an image that would have been acquired by the image acquisition unit, if a fluid bolus corresponding to the combination bolus would have been generated by using the same first location, second location and time between the end of the generation of the fluid bolus and the acquisition of the image as for all other images of the series of images, and b) a control image that would have been acquired by the image acquisition unit, if a fluid bolus corresponding to a control fluid bolus comprising only one labeling state would have been generated by using the same first location, second location and time between the end of the generation of the fluid bolus and the acquisition of the image as for all images of the series of images. Therefore, the combination image is indicative of a respective combination bolus and a combination sub-bolus of a combination bolus can be regarded as having also a post-labeling delay time being a time between a virtual end of a virtual generation of the combination sub-bolus and a virtual acquisition time of the image which in combination with the control image results in the combination image which is indicative of the combination bolus comprising the combination sub-bolus.

The combination images are indicative of combination boli having the same temporal length, i.e. the same length between a first end and a second end of the combination boli. For this reason and since the combination images can be regarded as resulting from a combination of images having been acquired at a respective acquisition time after the end of a virtual generation of a combination bolus or control bolus, respectively, wherein the acquisition time is the same for each combination of a combination image and combination bolus, the time between the second end of a combination sub-bolus and the second end of the combination bolus is indicative of a post-labeling delay time for a corresponding sub-bolus and the time between the first end of a combination sub-bolus and the second end of the combination bolus is indicative of the inflow time. Changing the temporal length and therefore the second end of the combination sub-bolus leads to a change of the post-labeling delay time for the corresponding sub-bolus. The sub-bolus length determination unit therefore determines the sub-bolus length based on at least two combination images being indicative of combination sub-boli that can be regarded as having different post-labeling delay times.

It should be noted that in the expression "first labeling state" the term "first" does not refer to a temporally or spatially first state, but in this expression the term "first" is just used for distinguishing this labeling state from another labeling state which might be named "second labeling state". For instance, in an embodiment first and second labeling states can correspond to labeled and non-labeled. Moreover, it should be noted that in the expression "first combination image" the term "first" does not refer to a temporally or spatially first combination image, but in this expression the term "first" is just used for distinguishing this combination image from another combination image which is named "second combination image".

Since in an embodiment the sub-bolus length, i.e. the subject specific length, is determined based on at least two combination images that are indicative of combination sub-boli that can be regarded as having different post-labeling delays and/or different inflow times, the optimal subject specific length of the sub-bolus of the further fluid bolus can be determined. The combination images being indicative of the combination sub-boli being regarded as having different post-labeling delay times show different phases in the inflow of the labeled fluid into the tissue of interest. Based on these different inflow phases it can be automatically determined, which post-labeling delay time would be necessary for the labeled fluid to have completely entered the capillary bed in all regions of the tissue of interest, so that, for instance, later perfusion measurements based on the series of medical images will not be corrupted by ATD artifacts. This correction (or adaption) of the acquisition of images can be performed during the acquisition of the series of images, based on the already acquired images of the series.

In an embodiment the image acquisition unit is adapted to acquire the series of images at the second location such that these images and also the first and second combination images show a tissue of interest, wherein the sub-bolus length determination unit is adapted to a) determine a first parameter, which is indicative of the amount of fluid, which has a first labeling state, in the tissue of interest shown in the first combination image, based on the first combination image and a second parameter, which is indicative of the amount of fluid, which has the first labeling state, in the tissue of interest shown in the second combination image, based on the second combination image, and b) determine the sub-bolus length based on the first and second parameters. Since the sub-bolus length determination unit is adapted to determine from the combination images a first parameter and a second parameter being indicative of the amount of fluid, which has the first labeling state, shown in the combination images having entered the tissue of interest and to determine the sub-bolus length based on these parameters, it is possible to determine the sub-bolus length, i.e. the subject specific length, based on information about the inflow of the fluid that can be obtained from the already acquired images forming the combination images.

The sub-bolus length can be determined in a step wise manner to step wise reach an optimal subject specific sub-bolus length. In an embodiment in each step a further image of the series of images is acquired and based on a first combination image and a second combination image, which results from a combination of the further image with at least one of the previously acquired images, a further sub-bolus length is determined. Repeating this step the sub-boli length iteratively converges in each step to an optimal subject specific sub-bolus length.

In an embodiment the tissue of interest is a capillary bed and the sub-bolus length determination unit is adapted to determine the sub-bolus length such that a) it is smaller than the length of a first sub-bolus of the fluid bolus, to which the image of the series of images corresponds, which is acquired immediately before the further image is acquired, if the first parameter is larger than the second parameter, and/or b) it is larger than the length of a first sub-bolus of the fluid bolus, to which the image of the series of images corresponds, which is acquired immediately before the further image is acquired, if the first parameter is smaller than the second parameter. If the first parameter is larger than the second parameter, i.e. if the first combination image shows a larger amount of fluid, which has the first labeling state, in the capillary bed than the second combination image, it can be assumed that the combination sub-bolus of the first combination image has not completely entered the capillary bed, which indicates that the post-labeling delay time of this combination sub-bolus is too small. In order to increase the post-labeling delay time, the length of the sub-bolus can be determined such that it is smaller than the length of a first sub-bolus of the fluid bolus, to which the image of the series of images corresponds, which is acquired immediately before the further images are acquired. Correspondingly, if the first parameter is smaller than the second parameter, i.e. if the first combination image shows a smaller amount of fluid, which has the first labeling state, in the capillary bed than the second combination image, it can be assumed that the combination sub-bolus of the first combination image has completely entered the capillary bed and might even in part have lost its labeling, e.g. by decay or suchlike, which indicates that the post-labeling delay time of this combination sub-bolus is too large. In order to decrease the post-labeling delay time, the length of the sub-bolus can be determined such that it is larger than the length of a first sub-bolus of the fluid bolus, to which the image of the series of images corresponds, which is acquired immediately before the further images are acquired In an embodiment the sub-bolus length determination unit is adapted to determine the sub-bolus length depending on a ratio of the first and second parameters. In particular, in an embodiment the tissue of interest is the capillary bed and the sub-bolus length determination unit is adapted to determine the sub-bolus length such that a) it is smaller than the length of a first sub-bolus of the fluid bolus, to which the image of the series of images corresponds, which is acquired immediately before the further image is acquired, if the ratio is smaller than a predefined threshold, and/or b) it is larger than the length of a first sub-bolus of the fluid bolus, to which the image of the series of images corresponds, which is acquired immediately before the further image is acquired, if the ratio is larger than a predefined threshold. The predefined threshold can be, for instance, 0.9 or it can have another threshold value. Since the parameter is indicative of the amount of fluid, which has the first labeling state, in the capillary bed shown in the respective combination image, the ratio of the first and second parameters is a measure for differences in the inflow state of the fluid, which has the first labeling state, with respect to the situations represented by the different combination images, wherein this information about the inflow state can be used for determining the length of the further sub-bolus.

In an embodiment the sub-bolus length determination unit is adapted to determine the first parameter based on the number of image elements of the first combination image having an image value being larger than a threshold in the first combination image and to determine the second parameter based on the number of image elements of the second combination image having an image value being larger than a threshold in the second combination image. The threshold can be a noise level of a respective combination image. Moreover, the sub-bolus length determination unit can be adapted to generate a histogram of the image values in the respective combination image and to determine a smallest maximum image value of the histogram as the threshold. The smallest maximum image value of the histogram is the smallest image value at which the histogram has a maximum. Thus, if the histogram has several maxima at different image values, the smallest of these image values is the smallest maximum image value.

When the fluid, which has the first labeling state, has reached the capillary bed, the fluid, which has the first labeling state, causes MR signals in a wide area in the tissue of interest, which leads to a relatively large number of image elements having an image value being larger than the threshold, especially larger than a noise level. If the fluid, which has the first labeling state, has not yet entered the capillary bed, the fluid, which has the first labeling state, can be found in the arteries only, wherein the arteries cover a relatively small area in comparison to the area covered by the capillary bed. Thus, although the MR signal caused by fluid, which has the first labeling state, in the arteries might be stronger than the MR signal caused by fluid, which has the first labeling state, in the capillary bed, the fluid, which has the first labeling state, in the arteries leads to a relatively small number of image elements having image values above the threshold. The number of image elements having image values above the threshold is therefore a good measure for indicating how much fluid, which has the first labeling state, has already entered the capillary bed. In other embodiments other types of parameters being indicative of the amount of fluid, which has the first labeling state, in the capillary bed shown in the respective combination image can be used. For instance, the entropy of the respective combination image can be determined for determining the respective parameter.

Preferentially the bolus generating unit is adapted to generate the fluid boli, to which the images correspond, such that they are representable by a matrix, wherein each row of the matrix represents a respective fluid bolus, wherein a sub-bolus, which has a first labeling state, of a fluid bolus is represented by a) one or several matrix elements having a same matrix value indicating the first labeling state or b) a single matrix element indicating the first labeling state, wherein a sub-bolus, which has a second labeling state, of a fluid bolus is represented by a) one or several matrix elements having a same matrix value indicating the second labeling state or b) a single matrix element indicating the second labeling state. Preferentially the matrix is a Hadamard matrix or a matrix comprising rows of a Hadamard matrix and an inserted additional row, wherein the additional row is generated by using a neighboring row of the Hadamard matrix, wherein matrix values indicating the first labeling state are replaced by matrix values indicating the second labeling state and vice versa. The Hadamard matrix is preferentially a non-mirrored Walsh-ordered Hadamard matrix or a Walsh-ordered Hadamard matrix mirrored left to right. The use of these matrixes can improve the imaging process. For instance, it can be possible to have acquired images, which allow the generation of the first combination image and the second combination image, at a relatively early point in time while acquiring the series of images. The additional row can be, for instance, inserted into the Hadamard matrix in between the second and third row of the Hadamard matrix, wherein in this case a first combination image may be generated based on the first image and the second image of the series of images and the second combination image may be generated based on the first image and the third image of the series of images. Thus, already after having acquired three images a length of a sub-bolus of a fluid bolus for a next image to be acquired can be determined.

Each sub-bolus represented by several matrix elements having the same matrix value can be regarded as consisting of several sub-sub-boli, wherein a single sub-sub-bolus is represented by a single matrix element. The length of a sub-bolus represented by several matrix elements having a same matrix value can be modified by modifying the length of one or several sub-sub-boli of the sub-bolus and/or by modifying the number of the sub-sub-boli. In an embodiment a length of a sub-sub-bolus represented by a matrix element in a certain column can only be modified, if earlier fluid boli do not have a sub-bolus represented by a single matrix element of the same certain column.

The matrix has preferentially two matrix values, wherein a first matrix value, which might be +1 or −1, indicates the first labeling state and a second matrix value, which might be −1 or +1, indicates the second labeling state.

In a further aspect of the present invention an imaging method for generating a series of images of a subject is presented, wherein the imaging method comprises:
  generating fluid boli at a first location of the subject by a bolus generating unit, wherein each fluid bolus comprises a sequence of sub-boli, wherein each sub-bolus has one of at least two different labeling states,
  acquiring images of the series of images at a second location of the subject by an image acquisition unit, after the fluid boli have been flowed from the first location to the second location, wherein each image corresponds to a respective fluid bolus, and
  determining a sub-bolus length based on at least one image of the acquired images of the series of images by a sub-bolus length determination unit,
  generating a further fluid bolus comprising a sequence of sub-boli at the first location by the bolus generating unit, wherein at least one of the sub-boli has the determined sub-bolus length, and
  acquiring a further image of the series of images at the second location of the subject by the image acquisition unit, after the further fluid bolus has been flowed from the first location to the second location.

In a further aspect of the present invention a computer program is presented, wherein the computer program comprises program code means for causing an imaging system as defined in claim 1 to carry out the steps of the imaging method as defined in claim 16, when the computer program is run on a computer controlling the imaging system.

It shall be understood that the imaging system of claim 1, the imaging method of claim 16 and the computer program of claim 17 have similar and/or identical preferred embodiments as defined in the dependent claims.

It shall be understood that a preferred embodiment of the invention can also be any combination of the dependent claims with the respective independent claim.

FIG. 1 shows schematically and exemplarily an embodiment of an imaging system 100 for generating a series of images of a patient 103. The imaging system 100 comprises a bolus generating unit 112 for generating a fluid bolus at a first location of the patient 103, wherein each fluid bolus has in this embodiment the same temporal length and comprises a sequence of sub-boli and wherein each sub-bolus has in this embodiment one of two different labeling states being either labeled or non-labeled. In this embodiment the first location is the neck of the patient 103 and the fluid is the blood of the patient.

The imaging system 100 further comprises an image acquisition unit 101 for acquiring images of the series of images at a second location of the patient 103 at a respective acquisition time, after the fluid boli have been flowed from the first location to the second location, wherein each image corresponds to a respective fluid bolus and wherein the difference between the time of generating a respective fluid bolus and the acquisition time for acquiring the respective image is in this embodiment the same for all combinations of a respective image and a corresponding respective fluid bolus. In this embodiment the second location is the head 102 of the patient 103.

In this embodiment the image acquisition unit 101 is adapted to generate MR images and the bolus generating unit 112 is adapted to generate the fluid boli such that labeled sub-boli are visible in the MR images. In particular, the bolus generating unit 112 is adapted to generate a labeled sub-bolus by magnetically marking a respective part of the blood and to generate a non-labeled sub-bolus by not magnetically marking the respective part of the blood.

The labeling can, e.g., be achieved by an inversion or saturation or other manipulation of the flip angle of the magnetization of the blood water. An exemplary description can be found, e.g. in the articles "Perfusion Imaging" by J. A. Detre et al., Magnetic Resonance in Medicine, volume 23, pages 37 to 45 (1992), "Magnetic resonance imaging of perfusion using spin inversion of arterial water" by D. S. Williams et al., Proceedings of the National Academy of Sciences, USA, volume 89, pages 212 to 216 (1992), "Continuous flow-driven inversion for arterial spin labelling using pulsed radio frequency and gradient fields" by W. Dai et al., Magnetic Resonance in Medicine, volume 60, issue 6, pages 1488 to 1497 (2008), the above mentioned article "Walsh-Ordered Hadamard Time-Encoded Pseudocontinuous ASL (WH pCASL)" by F. von Samson-Himmelstjerna et al. and in the U.S. Pat. No. 8,260,396, which are herewith incorporated by reference.

The sequence of sub-boli can then be achieved by switching between labeling and non-labeling using, for example, the pCASL technique, which is e.g. disclosed in the above mentioned article "Continuous flow-driven inversion for arterial spin labelling using pulsed radio frequency and gradient fields" by W. Dai et al., Magnetic Resonance in Medicine, volume 60, issue 6, pages 1488 to 1497 (2008). Different ways to time this switching are for instance described in the above mentioned articles "Highly efficient accelerated acquisition of perfusion inflow series by Cycled Arterial Spin Labeling" by M. Guenther, Proceeding of the 15th Annual Meeting of ISMRM, volume 15, page 380 (2007), "Volumetric measurement of Perfusion and Arterial Transit Delay using Hadamard Encoded Continuous Arterial Spin Labeling" by W. Dai et al., Magnetic Resonance in Medicine, volume 69, pages 1014 to 1022 (2012) and "Walsh-Ordered Hadamard Time-Encoded Pseudocontinuous ASL (WH pCASL)", by F. von Samson-Himmelstjerna et al., Magnetic Resonance in Medicine (2015) and the above mentioned U.S. Pat. No. 8,260,396, where different kinds of Hadamard matrixes are used for the encoding and decoding of the images.

The imaging system 100 comprises a control and processing device 104 including a controlling unit 105 for controlling the image acquisition unit 101 and the bolus generating unit 112 such that the fluid boli are generated and a corresponding series of images is acquired. Since a sub-bolus is generated by, for instance, applying a magnetic field at the first location for a certain time period, each sub-bolus has a spatial length and also a temporal length, wherein the temporal length is defined by the time period of applying the magnetic field. In this embodiment the temporal sub-bolus length is determined.

Figure 2:
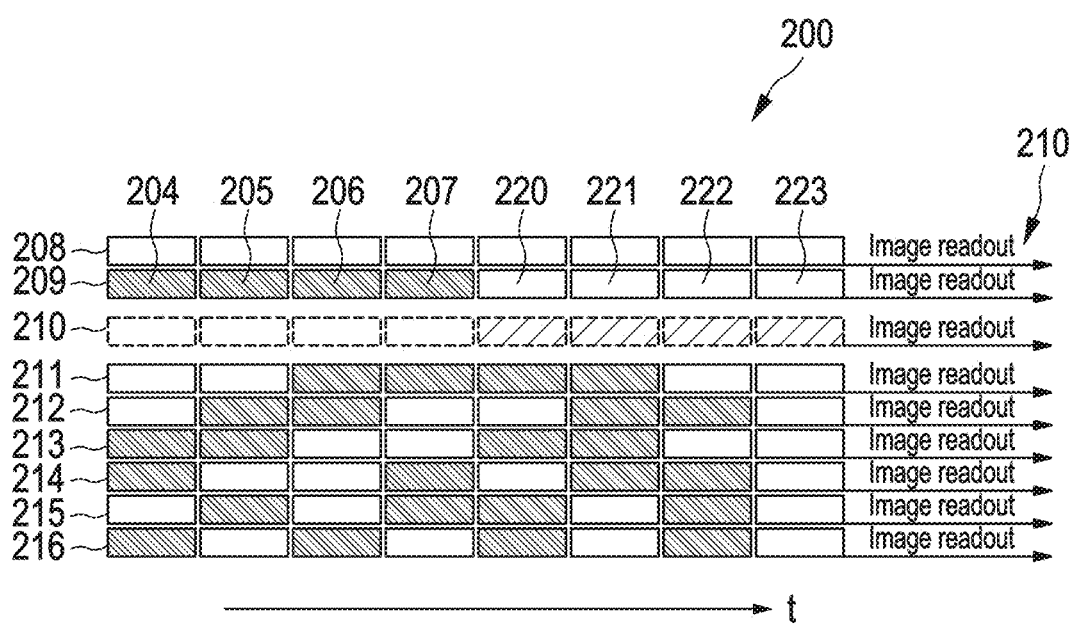
FIG. 2 shows an example of a matrix encoding a series of fluid boli to be used for acquiring the series of images.

The bolus generating unit 112 is adapted to generate the fluid boli such that they are representable by a matrix 200 which is schematically and exemplarily shown in FIG. 2. Each row of the matrix 200 represents a respective fluid bolus, wherein in this embodiment a labeled sub-bolus of a fluid bolus is represented by one or several matrix elements having a same matrix value indicating labeling and wherein a non-labeled sub-bolus of a fluid bolus is represented by one or several matrix elements having a same matrix value indicating non-labeling. In FIG. 2 black boxes indicate labeling and white boxes indicate non-labeling. After the respective fluid bolus has been generated at the first location, a predetermined time is waited before acquiring the corresponding image at the second location as indicated by the arrows 210. The first row 208 of the matrix 200 represents a fluid bolus being completely non-labeled. The second row 209 represents a fluid bolus comprising a first labeled sub-bolus and a second non-labeled sub-bolus, wherein the first labeled sub-bolus is represented by the four matrix elements 204 . . . 207 and the second non-labeled sub-bolus is represented by four matrix elements 220 . . . 223. The sub-boli of the second row can therefore also be regarded as being assembled of four sub-sub-boli having the same labeling state respectively, wherein the sub-sub-boli can be regarded as representing a single matrix element being either labeled or non-labeled.

The matrix 200 comprises rows 208, 209 and 211 . . . 216 of a Hadamard matrix and an inserted additional row 210, wherein the additional row 210 is generated by using the second row 209 of the Hadamard matrix, wherein matrix values of the second row 209 indicating labeling are replaced by matrix values indicating non-labeling and vice versa. In this sense the additional row 210 can be regarded as being an inversion of the second row 209.

The matrix 200 defines a sequence of labeled and non-labeled sub-boli of a respective fluid bolus, but the matrix 200 does not define the temporal length and hence also not the spatial length of the respective sub-bolus or the sub-sub-boli forming the sub-bolus. In this embodiment the length of a sub-bolus is defined by the lengths and the number of one or several sub-sub-boli represented by a respective single matrix element. For instance, the length of the first labeled sub-bolus comprising sub-sub-boli represented by matrix elements 204 . . . 207 can be defined by the lengths of these sub-sub-boli.

The lengths of the sub-sub-boli of, for instance, the first, second and third fluid boli can be predefined and fixed, wherein, when the corresponding first, second and third images have been acquired, the lengths of the sub-sub-boli and hence of sub-boli of fluid boli, which will be used for acquiring further images of the series of images, can be determined based on the already acquired images of the series of images, wherein in this embodiment the determination can be regarded as changing the length of the sub-sub-bolus relative to the predefined length. This determination of the lengths of the sub-sub-boli and hence of the sub-boli formed by the sub-sub-boli preferentially considers the rule that all sub-sub-boli represented by matrix elements of a same column of the matrix 200 should have the same length. This means that, if a fluid bolus is generated, which comprises a sub-bolus represented by a single matrix element of a certain column, sub-sub-boli of following fluid boli, which are represented by matrix elements of the same certain column, need to have the length of the sub-bolus represented by the single matrix element.

In FIG. 2 the first row 208 of the matrix 200 represents a completely non-labeled fluid bolus, wherein this first fluid bolus defines the total length for all following fluid boli, i.e. the sum of all lengths of all sub-sub-boli of a respective fluid bolus represented by a respective row of the matrix 200 needs to be same for each following fluid bolus.

After the second fluid bolus has been generated, which is represented by the second row 209 of the matrix 200, the total length of the first sub-sub-boli 204 . . . 207 is defined and fixed for the following fluid boli represented by the following rows of the matrix 200. Correspondingly, the total length of the sub-sub-boli 220 . . . 223 defines a fixed total length of the corresponding sub-sub-boli in the following fluid boli represented by the further rows of the matrix 200. The length of a single sub-sub-boli is still not fixed and can be determined for the following fluid boli.

Referring again to FIG. 1, the imaging system 100 further comprises a combination unit 106 for generating a combination image by combining at least two of the already acquired images, wherein the combination image is indicative of a combination fluid bolus being indicative of a combination of the fluid boli to which the at least two images correspond. The combination unit 106 is preferentially adapted to generate a combination image by adding and/or subtracting several images from each other. For instance, after a first image and a second image have been acquired, these two images can be subtracted from each other, in order to generate a combination image. If a first image, a second image, a third image and a fourth image should be combined, it is possible that, for instance, the first and second images are added to each other and that then the third image and the fourth image are subtracted from the resulting sum image. The blood boli of the acquired images are combined correspondingly, i.e. for instance, if a first image and a second image are subtracted from each other, also the generated fluid boli represented by the respective rows of the matrix 200 are subtracted from each other.

The combination images can be regarded as images that would result from a combination of an image that would have been acquired by the image acquisition unit, if a fluid bolus corresponding to the combination bolus would have been generated by using the same first location, second location and time between the end of the generation of the fluid bolus and the acquisition of the image as for all other images of the series of images, and a control image that would have been acquired by the image acquisition unit, if a fluid bolus corresponding to a control fluid bolus comprising only a non-labeling state would have been generated by using the same first location, second location and time between the end of the generation of the fluid bolus and the acquisition of the image as for all images of the series of images. The combination bolus can therefore be regarded as a fluid bolus as used in a standard multi-TI method and the combination image can therefore also be regarded as one of the images resulting from the standard multi-TI method. The combination bolus has the same total length as the really generated fluid boli.

For instance, for a $2''\times2''$ Hadamard matrix H the decoding is achieved by adding or subtracting the encoded images according to the entries of the encoding matrix (e.g. '1'='add' and '−1'='subtract'). In other words, the encoding matrix also yields the decoding prescription. This is possible because H is orthogonal and symmetric and, therefore, $H=H^1$. See also the above mentioned article "Walsh-Ordered Hadamard Time-Encoded Pseudocontinuous ASL (WH pCASL)" by F. von Samson-Himmelstjerna et al.

The respective temporal length of a respective fluid bolus can be defined relative to the respective acquisition time, wherein a first end of a respective temporal length has a larger distance to the respective acquisition time than a second end of the respective temporal length and wherein this relative temporal length is the same for different fluid boli and for a combination bolus being indicative of the combination of several fluid boli. The combination unit 106 is adapted to generate a first combination image by combining at least two of the already acquired images of the series of images such that it is indicative of a first combination bolus 500 including a single labeled combination sub-bolus 510 only and to generate a second combination image by combining at least two of the acquired images such that it is indicative of a second combination bolus 505 including a single labeled combination sub-bolus 511 only. The combination sub-boli 500, 505 are schematically and exemplarily illustrated in FIG. 3.

Figure 3:
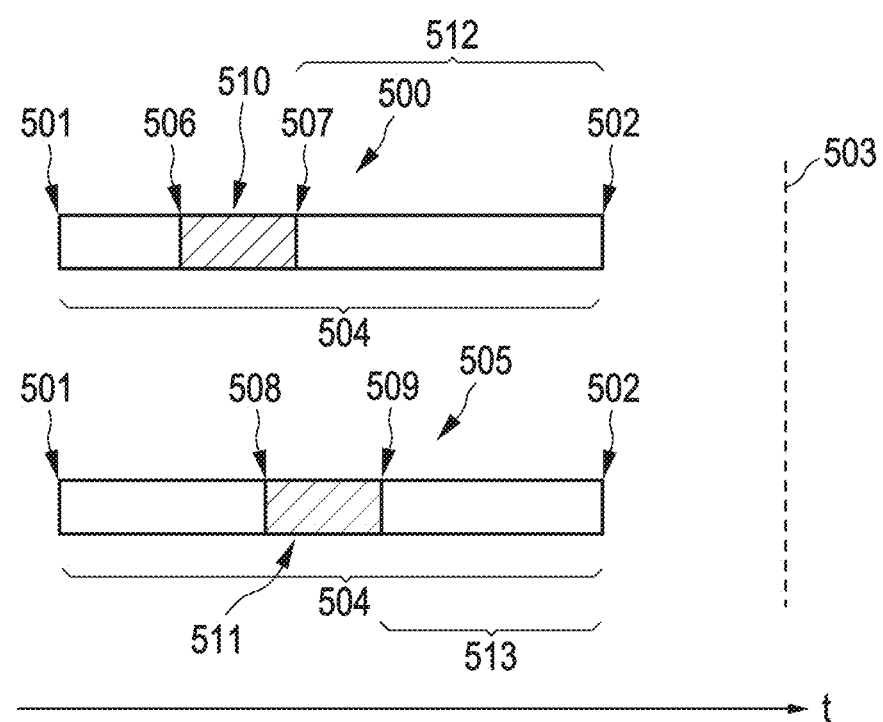
FIG. 3 illustrates schematically and exemplarily two combination fluid boli.

As can be seen in this FIG. 3, the temporal length 504 is the same for both combination boli 500, 505, wherein the respective first end 501 has a larger temporal distance to the acquisition time 503 than the respective second end 502. Each of the single labeled combination sub-boli 510, 511 has first and second ends 506, 507, wherein the first end 506 of the single labeled combination sub-bolus 510 of the first combination bolus 500 is closer to the first end 501 of the first combination bolus 500 than the second end 507 of the single labeled combination sub-bolus 510. The first end 508 of the single labeled combination sub-bolus 511 of the second combination bolus 505 is closer to the first end 501 of the second combination bolus 505 than the second end 509 of the single labeled combination sub-bolus 511. The combination unit 106 is adapted to generate the first and second combination boli 500, 505 such that a first temporal distance 512 between a) the second end 507 of the single labeled combination sub-bolus 510 of the first combination bolus 500 and b) the second end 502 of the first combination bolus 500 is larger than a second temporal distance 513 between a) the second end 509 of the single labeled combination sub-bolus 511 of the second combination bolus 505 and b) the second end 502 of the second combination bolus 505.

The imaging system 100 further comprises a sub-bolus length determination unit 107 for determining a temporal sub-bolus length based on the generated first and second combination images, wherein the determined sub-bolus length is a sub-bolus length of a fluid bolus used for generating a next image of the series of images. In particular, the sub-bolus length determination unit 107 is adapted to determined a first parameter, which is indicative of the amount of labeled blood in the capillary bed visible in the first combination image, based on the first combination image and a second parameter which is indicative of the amount of labeled blood in the capillary bed visible in the second combination image, based on the second combination image. The sub-bolus length determination unit 107 is further adapted to determine the sub-bolus length of a fluid bolus of a following image, which needs to be acquired next, based on the first and second parameters. Preferentially, the sub-bolus length determination unit 107 is adapted to determine the sub-bolus length such that it is smaller than the length of a first sub-bolus of the fluid bolus, to which the image of the series of images corresponds, which is acquired immediately before the further image is acquired, if the first parameter is larger than the second parameter, and such that it is larger than the length of the first sub-bolus, if the first parameter is smaller than the second parameter. The sub-bolus length determination unit 107 can also be adapted to determine the sub-bolus length depending on a ratio of the first and second parameters. For instance, the sub-bolus length determination unit 107 can be adapted to determine the sub-bolus length such that it is smaller than the length of a first sub-bolus of the fluid bolus, to which the image of the series of images corresponds, which is acquired immediately before the further image is acquired, if the ratio is smaller than a predefined threshold, and such that it is larger than the length of this first sub-bolus, if the ratio is larger than the predefined threshold. In the case of using the ratio for determining the sub-bolus length the predefined threshold is preferentially 0.9.

The sub-bolus length determination unit 107 is adapted to determine the first parameter based on the number of image elements of the first combination image having an image value being larger than a threshold in the first combination image and to determine the second parameter based on the number of image elements of the second combination image having an image value being larger than a threshold in the second combination image. Preferentially the thresholds in the first and second combination images are indicative of the noise levels in these images. In an embodiment the sub-bolus length determination unit 107 can be adapted to generate a histogram of the image values in the respective combination image and to determine a smallest maximum image value of the histogram as the threshold.

In the following the use of the imaging system 100 in the free lunch technique will be described, wherein the first sub-bolus of each fluid bolus is used for generating a perfusion image. In order to generate a high quality perfusion image, the timing of the generation of the fluid boli and the acquisition of the images of the series of images need to be adapted such that the first sub-boli of the fluid boli have completely entered the capillary bed of the brain, when the images are acquired.

The first combination bolus is preferentially generated such that, given the already acquired images and the correspondingly already used fluid boli, the single labeled combination sub-bolus has the longest possible temporal distance between its first end and the acquisition time, i.e. has the longest possible inflow time. The second combination bolus is preferentially generated such that the inflow time of the single labeled combination sub-bolus is smaller than the inflow time of the combination sub-bolus of the first combination bolus. Further, the first and second combination boli are preferably generated such that the single labeled combination sub-boli of the respective combination bolus have different temporal distances between the second end of the respective single labeled sub-bolus and the acquisition time, i.e. have different post-labeling delay times. Moreover, for generating the second combination bolus and hence the second combination image the lastly used fluid bolus and the correspondingly lastly acquired image, respectively, is preferentially used. For instance, if the sub-bolus length determination unit 107 is adapted to determine the sub-bolus length of the first sub-bolus of the fluid bolus represented by the fifth row 212 of the matrix 200, the second combination image is preferentially generated by combining the fourth image, which corresponds to the fluid bolus represented by the fourth row 211 of the matrix 200, with at least one of the other images which have already been acquired.

If the first parameter is larger than the second parameter, i.e. for instance, if the number of image elements above noise level in the first combination image is larger than the number of image elements above noise level in the second combination image, this indicates that not the entire first sub-bolus of the immediately before generated fluid bolus has entered the capillary bed. In this case the temporal length of the first sub-bolus of the fluid bolus to be generated next is determined such that it is shorter than the length of the first sub-bolus of the fluid bolus generated lastly, in order to prolong the post-labeling delay time for the first sub-bolus. If the first parameter is smaller than the second parameter, i.e., for instance, if the number of image elements above noise level in the first combination image is smaller than the number of image elements above noise level in the second combination image, this indicates that the first sub-bolus of the fluid bolus, which has been generated lastly, has completely entered the capillary bed of the brain and might even already have lost its labeling, e.g. by decay or suchlike processes. In this case the temporal length of the first sub-bolus of the fluid bolus to be generated next is determined such that it is longer than the length of the first sub-bolus of the fluid bolus just generated, in order to shorten the post-labeling delay time.

In the following an example for generating fluid boli and acquiring images will be described with reference to FIG. 4, wherein in this example the matrix 200 described above with reference to FIG. 2 is used.

Figure 4:
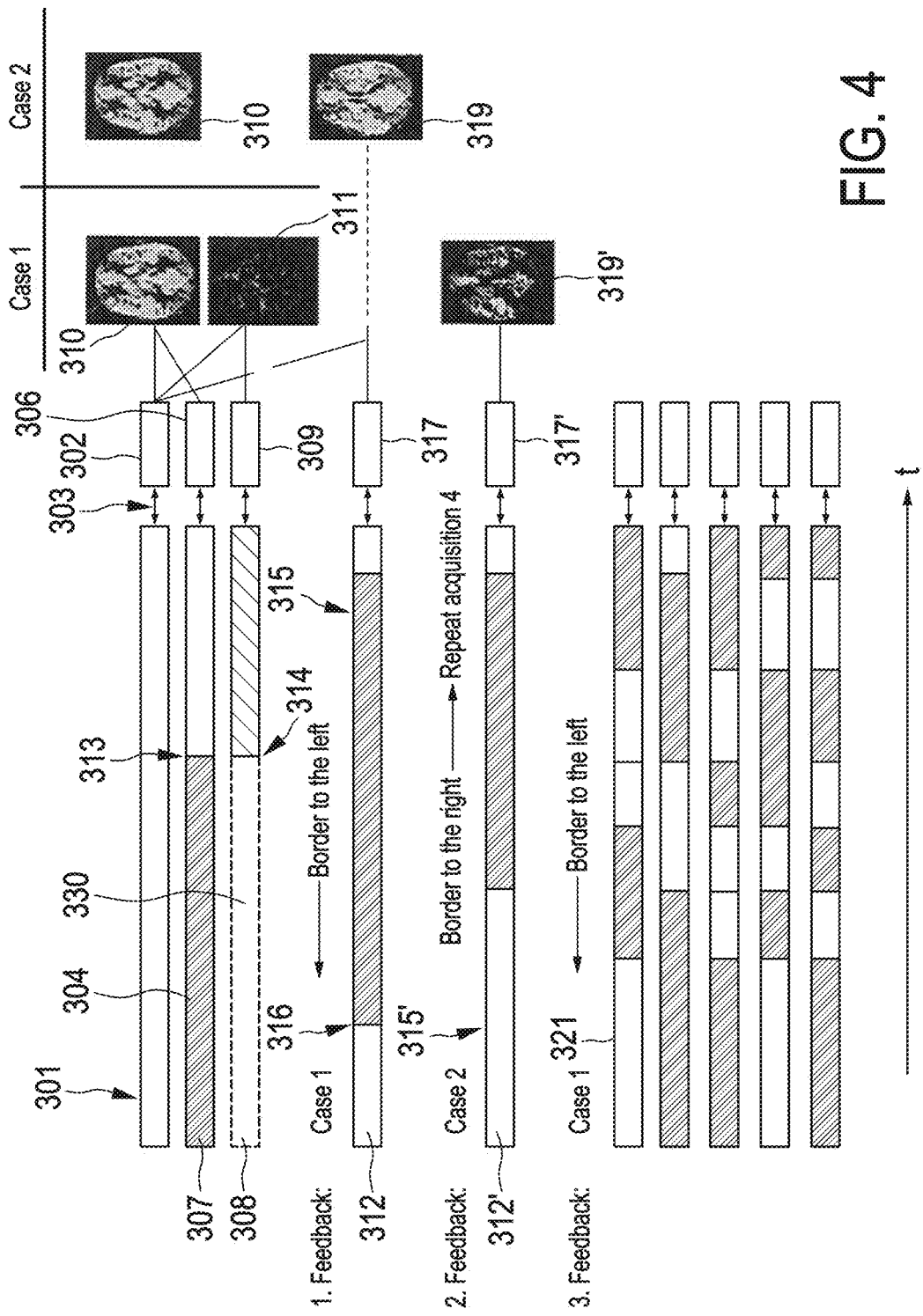
FIG. 4 illustrates schematically and exemplarily several fluid boli and images which have been acquired by using the fluid boli.

In FIG. 4 a first fluid bolus 301 corresponds to the first row 208 of the matrix 200 and hence is completely non-labeled. The fluid generating unit 112 generates the first fluid bolus 301 at the first location and the image acquisition unit 101 acquires a first image 302 at the second location after waiting for a predefined time 303. The first image 302 corresponds to the first fluid bolus 301.

The second fluid bolus 307 is represented by the second row 209 of the matrix 200 and the third fluid bolus 308 is represented by the third row 210 of the matrix 200. The bolus generating unit 112 generates the second fluid bolus 307 at the first location. The second fluid bolus 307 flows to the second location where the image acquisition unit 101 acquires a second image 306 after waiting for a predefined time 303. Correspondingly, a third image 309 is acquired based on the third fluid bolus 308.

After the first three images 302, 306, 309 have been acquired and before acquiring the fourth image 317 based on the fourth fluid bolus 315 represented by the fourth row 211 of the matrix 200, the combination unit 106 subtracts the first image 302 from the second image 306 for generating a first combination image 310 and subtracts the first image 302 from the third image 309 for generating a second combination image 311. Moreover, the sub-bolus length determination unit 107 determines the length of the first sub-bolus 312 of the fourth fluid bolus 315 based on the first and second combination images 310, 311.

The first combination image 310 can be regarded as being indicative of a combination bolus comprising a combination sub-bolus having a second end at the relative time point 313, wherein this relative time point 313 is regarded as being relative to the respective acquisition time. The second combination image 311 can be regarded as being indicative of a combination bolus comprising a combination sub-bolus with a second end at the relative time point 314. Since the post-labeling delay time for a sub-bolus is defined as the time between the respective second end of the sub-bolus and the respective acquisition time, the first combination image 310 can be regarded as being indicative of a first post-labeling delay time and the second combination image 311 can be regarded as being indicative of a second post-labeling delay time, wherein the first post-labeling delay time is larger than the second post-labeling delay time. The combination images used for determining the length of the sub-bolus are therefore indicative of different post-labeling delay times.

If the first parameter, i.e. in this example the number of image values above the noise level in the first combination image 310 being indicative of the larger post-labeling delay time, is larger than the second parameter, i.e. in this example the number of image elements above the noise level in the second combination image having the shorter post-labeling delay time, the first sub-boli 304, 330 of the second and third fluid boli 307, 308 have reached the capillary bed but also show an additional contribution of blood that has not yet reached the capillary bed and is still in the arteries of the brain such that the post-labeling delay time for the first sub-bolus 312 of the fourth fluid bolus 315 to be generated next has to be longer than the post-labeling delay time of the first sub-bolus 330 of the third fluid bolus 308.

The first combination image 310 is indicative of the first combination bolus that in this example has the same labeling as the second fluid bolus 307 and the second combination image 311 is indicative of the second combination bolus that in this example has the same labeling as the third fluid bolus 308. The second combination image 311 being indicative of the second combination bolus comprising only one labeled combination sub-bolus, which has an inflow time that corresponds to the post-labeling delay time of the labeled combination sub-bolus of the first combination bolus, shows only labeled blood in the arteries. Therefore, the first combination image 310 not only shows labeled blood in the capillary bed, but also must show labeled blood that is still in the arteries. Thus the first sub-bolus 312 of the fourth fluid bolus 315 has to be shorter than the first sub-bolus 330 of the third fluid bolus 308.

In FIG. 4 this case is denoted as "case 1". The length of the first sub-bolus 312 of the further fluid bolus 315 is therefore shorter than the length of the first sub-bolus 330 of the third fluid bolus 308. The sub-bolus length determination unit 107 therefore determines the length of the first sub-bolus 312 of the fourth fluid bolus 315 to be generated next such that it is shorter than the length of the first sub-bolus 330 of the third fluid bolus 308. The second end 316 of the sub-bolus 312 is shifted to an earlier time in comparison to the second end 317 of the first sub-bolus 330, i.e. in FIG. 4 the border is shifted to the left.

Several attempts to prolong or shorten the sub-bolus length are possible. One possible attempt is to determine the first sub-bolus length such that is lies always in the middle of the previous two acquired first sub-boli, similar to a binary search algorithm. Another paradigmatic attempt is to determine the sub-bolus length according to the relative difference in the determined parameter of the different combination images. The higher the difference, the more the first sub-bolus duration will be prolonged/shortened.

After a fourth image 317 has been acquired, which corresponds to the fourth fluid bolus 315, a new second combination image 319 is generated by combining the fourth image 317 and the first image 302, i.e. in this example by subtracting the fourth image 317 from the first image 302. The sub-bolus length determination unit 107 determines the second parameter for the newly generated second combination image 319 and compares this second parameter with the first parameter determined for the first combination image 310. In this example the first parameter is smaller than the new second parameter denoted as "case 2" in FIG. 4, thereby indicating that the fourth labeling delay of the first sub-bolus 312 of the fourth fluid bolus 315 is too long such that the sub-bolus length determination unit 107 determines the first sub-bolus 312' of the next fluid bolus 315' such that the length is larger than the length of the first sub-bolus 312 of the fourth fluid bolus 315. This next fluid bolus 315' can be regarded as being a replacement of the original fourth fluid bolus 315, i.e. this further fluid bolus 315' is also represented by the fourth row of the matrix 200 and in the following the new fluid bolus 315' and the new image 317', which corresponds to the new fluid bolus 315', are regarded as being the fourth fluid bolus and the fourth image of the series of images. Correspondingly, a new second combination image 319' is generated by subtracting the first image 302 from the new fourth image 317'.

Using new fourth image 317' to generate the next combination image, in this embodiment according to the above described method it is determined that the first sub-bolus 321 of the fifth row has to be shortened again as indicated by the arrow. After application of a fluid bolus corresponding to the fifth row and acquisition of the fifth image all sub-sub-boli lengths have been determined. The acquisition of the remaining images of the series of images corresponding to the sixth to ninth matrix row has therefore to be performed without further adapting the sub-boli length.

Before generating a next respective fluid bolus a respective new second combination image is generated and a respective new second parameter is determined, wherein based on this new second parameter and the first parameter a length of the first sub-bolus of a following fluid bolus to be generated is determined. This procedure of determining the length of the next first sub-bolus, generating the corresponding next fluid bolus and acquiring the corresponding next image is repeated, until an abort criterion is fulfilled. This abort criterion might be, for instance, that for each row of the matrix 200 an image has been acquired, that a difference between the first parameter and the second parameter is smaller than a predetermined threshold, et cetera.

The imaging system further comprises a matrix providing unit 108 for allowing a user to select one of a plurality of possible matrixes defining the frame for the acquisition of the series of images. Moreover, the imaging system 100 comprises a processing unit 109 for processing the series of medical images, for instance, in order to determine a perfusion image based on the series of acquired images using one of the known methods as described, for instance, in the above mentioned articles "Time-Encoded pseudoContinuous Arterial Spin Labeling: Basic Properties and Timing Strategies for Human Applications" by W. M. Teeuwisse et al. and "Walsh-Ordered Hadamard Time-Encoded Pseudo-continuous ASL (WH pCASL)", by F. von Samson-Himmelstjerna et al.

The imaging system 100 further comprises an input unit 110 like a keyboard, a computer mouse, a touchpad, et cetera for, for instance, allowing a user to select a desired matrix, to start an imaging procedure, et cetera, and an output unit 111 like a display for, for instance, showing the acquired images and the result of the processing of the acquired images like a perfusion image.

Figure 5:
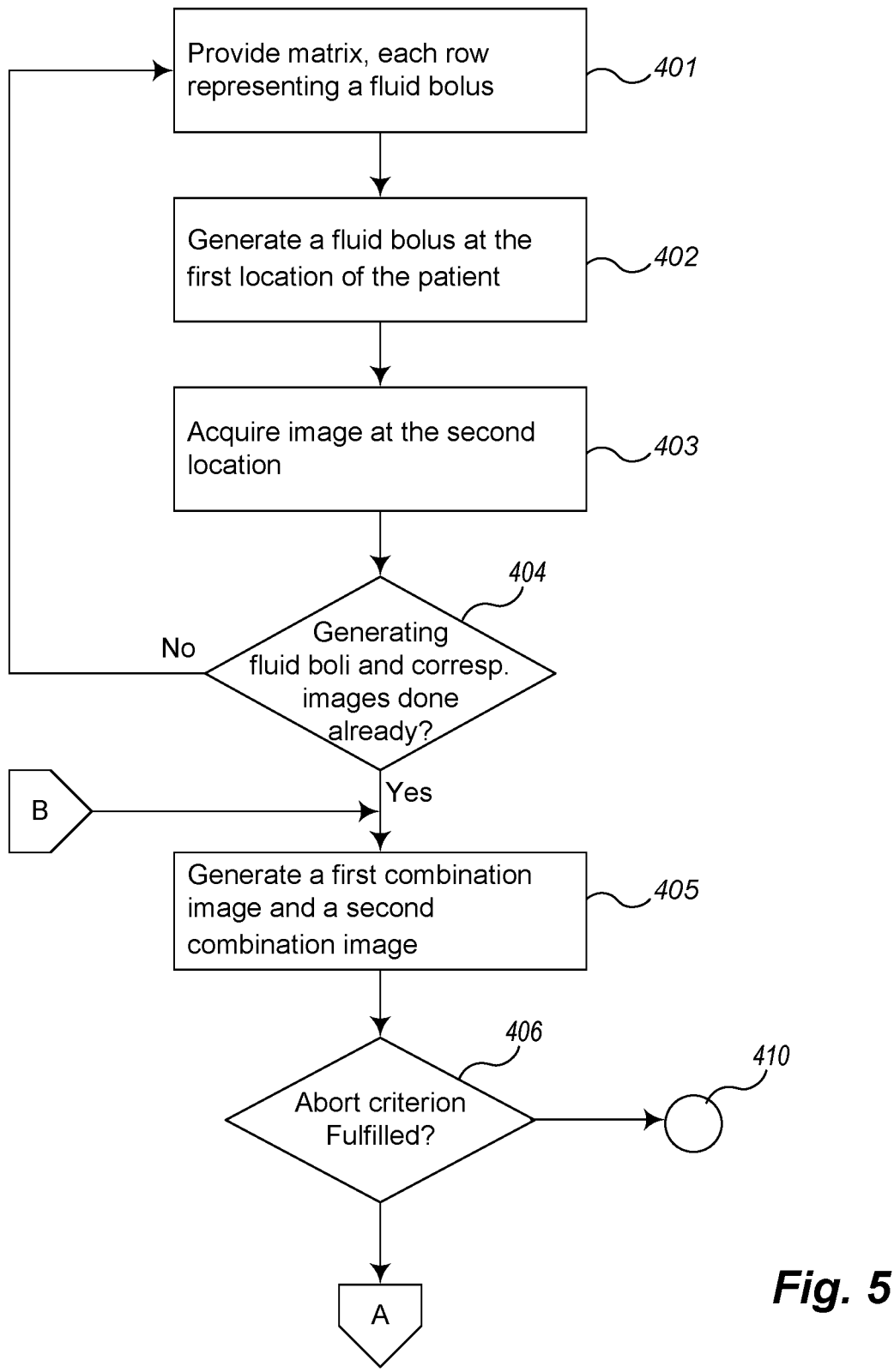
FIG. 5 shows a flowchart exemplarily illustrating an embodiment of an imaging method for generating a series of images.

In the following an embodiment of an imaging method for generating a series of images of patient will exemplarily be described with reference to a flow chart shown in FIG. 5.

In step 401 a matrix is provided, wherein each row of the matrix represents a fluid bolus comprising a sequence of sub-boli, wherein each sub-bolus is either labeled or non-labeled. A labeled sub-bolus of a fluid bolus is represented by one or several matrix elements having a same matrix value indicating labeling, and a non-labeled sub-bolus of a fluid bolus is represented by one or several matrix elements having a same matrix value indicating non-labeling. The matrix just defines the sequence of labeling and non-labeling of the respective fluid bolus, but not the length of the respective sub-bolus and also not of the entire respective fluid bolus length. However, in the following steps all fluid boli will have the same length and the length of the sub-boli is defined by the number and length of sub-sub-boli represented by single matrix elements indicating either labelling or non-labelling.

In step 402 a fluid bolus is generated at the first location of the patient by the bolus generating unit, wherein at the beginning a first fluid bolus is generated in accordance with the first row of the provided matrix. In step 403 an image of the series of images is acquired at the second location by the image acquisition unit, after the respective fluid bolus has been flowed from the first location to the second location. In step 404 it is checked whether the steps of generating fluid boli and acquiring corresponding images have already been performed such that the first three images have been generated. If this is the case, the method continues with step 405. Otherwise, the method continues with step 402.

In step 405 the already acquired images are used for generating a first combination image and a second combination image, wherein the first combination image is indicative of a first combination fluid bolus being indicative of a combination of the fluid boli to which at least two images correspond, which have been used for generating the first combination image, and wherein the second combination image is indicative of to a second combination fluid bolus being indicative of a combination of the fluid boli to which at least two images correspond, which have been used for generating the second combination image.

In step 406 it is determined whether an abort criterion is fulfilled, wherein, if this is the case, the method ends in step 410. Otherwise, the method continues with step 407. The abort criterion is, for instance, that the above mentioned first parameter, which can be determined based on the first combination image, and the above mentioned second parameter, which can be determined based on the second combination image, differ by less than a predefined threshold.

In step 407 the sub-bolus length determination unit determines a length of a first sub-bolus of a next fluid bolus, which according to the provided matrix is to be generated, based on the generated first and second combination images. In step 408 the next fluid bolus is generated such that the first sub-bolus has the determined length and in step 409 a corresponding next image is acquired. The method then continues with step 405, wherein now only a new second combination image is generated by combining the newly acquired image with one of the previously acquired images.

While performing this imaging method, the borders of the sub-sub-boli, i.e. the length of the sub-sub-boli or, in other words, the width of the columns of the matrix, become more and more constrained, wherein earlier during the acquisition of the series of images these borders are adjustable such that, for instance, the first sub-bolus has a length which allows the respective first sub-bolus to completely enter the capillary bed, wherein the labeling signal of the first sub-bolus is still relatively strong, thereby allowing for determining a high quality perfusion image.

Although in the embodiments described above with reference to FIGS. 1 to 5 the images are MR images, in other embodiments the images can be images acquired by another imaging modality like a computed tomography imaging modality, wherein in this case the labeling is performed by using a label being visible by the respective imaging modality. For instance, in case of computed tomography contrast agents like iodine based contrast agents can be used for generating fluid boli having sequences of sub-boli which have one of at least two different labeling states.

Although in the embodiments described above with reference to FIGS. 1 to 5 the tissue of interest is the brain, in other embodiments other parts of a patient can be imaged, especially other kinds of tissue for which a perfusion image should be determined.

Although in the embodiments described above with reference to FIGS. 1 to 5 the sub-bolus length is determined based on two combination images, the sub-bolus length can also be determined based on one or more of the already acquired images without combining the images, or based on a single combination image for instance using the entropy of the combination image as parameter for determining the sub-bolus length.

Although in the embodiments described above with reference to FIGS. 1 to 5 a certain matrix has been used, in other embodiments other matrixes can be used, especially matrixes having other numbers of rows and/or columns. Preferentially the order of the matrix is larger than or equal to 8. In an embodiment the matrix is an N+1 (row)×N (column) matrix, wherein two neighboring rows of the matrix have inverted matrix values, i.e., if a matrix value of one of the neighboring rows in a certain column indicates a first labeling state, the matrix value of the other of the neighboring rows in the certain column indicates a second labeling state and vice versa, wherein in this embodiment the respective matrix value can either indicate the first labeling state or the second labeling state. In an embodiment the matrix is a Walsh ordered Hadamard matrix.

Although in embodiments described above with reference to FIGS. 1 to 5 the length of the first sub-bolus of a next fluid bolus to be generated has been determined, in other embodiments also the length of another sub-bolus of a next fluid bolus to be generated can be determined.

Although in the embodiments described above with reference to FIGS. 1 to 5 a sub-bolus is represented by several matrix elements indicating either labeling or non-labeling, it is also possible that each matrix element represents a respective single sub-bolus, i.e. that a sub-bolus is not formed by a sequence of sub-sub-boli, but that each matrix element is regarded as representing a respective single sub-bolus, wherein several sub-boli being labeled can be arranged side-by-side and several sub-boli being non-labeled can be arranged side-by-side.

Although in the described embodiments described above with reference to FIGS. 1 to 5 the acquisition of the images is optimized for improving a perfusion image, the optimization of the acquisition, especially of the determination of the respective length of a sub-bolus of a following fluid bolus, can be also optimized such that a correction of a T1 relaxation can be achieved. For example, to this end the length of the individual sub-sub-boli is chosen longer for longer post-labeling delay times. Hereby, the length of the individual sub-boli is determined by the T1-decay of labeled blood, such that for longer post-labeling delay times higher concentrations of labeled blood are generated which compensates the T1-decay. For this see e.g. the above mentioned article "Time-Encoded pseudoContinuous Arterial Spin Labeling: Basic Properties and Timing Strategies for Human Applications" by W. M. Teeuwisse et al.

Other variations to the disclosed embodiments can be understood and effected by those skilled in the art in practicing the claimed invention, from a study of the drawings, the disclosure, and the dependent claims.

In the claims the word "comprising" does not exclude other elements or steps, and the indefinite article "a" or "an" does not exclude a plurality.

A single unit or device may fulfill the functions of several items recited in the claims. The mere fact that certain measurements are recited in mutually different dependent claims does not indicate that a combination of these measures cannot be used to advantage.

Procedures like the generation of combination images, the determination of lengths of sub-boli, i.e. of temporal sub-bolus lengths, et cetera performed by one or several units or devices can be performed by any other number of units or devices. These procedures and/or the control of the imaging system in accordance with the imaging method can be implemented as program code means of a computer program and/or as the dedicated hardware.

A computer program may be stored/distributed on a suitable medium such as an optical storage medium or a solid state medium or a tangible computer-readable medium, supplied together with or as part of other hardware, but may also be distributed in other forms, such as via the internet or other wired or wireless telecommunication systems.

Any reference signs in the claims should not be construed as limiting the scope.

The invention claimed is:

1. An imaging system for generating a series of images of a subject, wherein the imaging system comprises:
   a bolus generating unit for generating fluid boli at a first location of the subject, wherein each fluid bolus comprises a sequence of sub-boli, wherein each sub-bolus has one of at least two different labeling states;
   an image acquisition unit for acquiring images of the series of images at a second location of the subject at a respective acquisition time, after the fluid boli have been flowed from the first location to the second location, wherein each image corresponds to a respective fluid bolus; and
   a sub-bolus length determination unit for determining a sub-bolus length based on at least one image of the acquired images of the series of images,
   wherein the bolus generating unit is configured to generate a further fluid bolus comprising a further sequence of sub-boli at the first location, wherein at least one of the sub-boli of the further sequence of sub-boli has the determined sub-bolus length, and
   wherein the image acquisition unit is configured to acquire a further image of the series of images at the second location of the subject, after the further fluid bolus has been flowed from the first location to the second location.

2. The imaging system of claim 1 wherein the imaging system further comprises a combination unit for generating a combination image by combining at least two of the acquired images, wherein the combination image is indicative of a combination fluid bolus being indicative of a combination of at least two fluid boli, wherein the sub-bolus length determination unit determines the sub-bolus length based on the generated combination image.

3. The imaging system of claim 2, further comprising:
   wherein the fluid boli have a same temporal length, wherein the difference between the time of generating a respective fluid bolus and the acquisition time for acquiring the respective image is the same for all combinations of the respective image and a corresponding respective fluid bolus;
   wherein the respective temporal length of the respective fluid bolus is defined relative to the respective acquisition time, wherein a first end of the respective temporal length has a larger distance to the respective acquisition time than a second end of the respective temporal length, wherein this relative temporal length is the same for different fluid boli and for a combination bolus being the combination of several fluid boli;
   wherein the combination unit is configured to generate a first combination image by combining at least two of the acquired images such that it is indicative of a first combination bolus only including a single combination sub-bolus, which has a first labeling state, and to generate a second combination image by combining at least two of the acquired images such that it is indicative of a second combination bolus only including a single combination sub-bolus, which has the first labeling state;
   wherein each of the single combination sub-boli, which have the first labeling state, has first and second ends, wherein the first end of the single combination sub-bolus, which has the first labeling state, of the first combination bolus is closer to the first end of the first combination bolus than the second end of the single combination sub-bolus, which has the first labeling state, wherein the first end of the single combination sub-bolus, which has the first labeling state, of the second combination bolus is closer to the first end of the second combination bolus than the second end of the single combination sub-bolus, which has the first labeling state;
   wherein a first temporal distance between a) the second end of the single combination sub-bolus, which has the first labeling state, of the first combination bolus and b) the second end of the first combination bolus is larger than a second temporal distance between a) the second end of the single combination sub-bolus, which has the first labeling state, of the second combination bolus and b) the second end of the second combination bolus, and/or wherein a third temporal distance between a) the first end of the single combination sub-bolus, which has the first labeling state, of the first combination bolus and b) the second end of the first combination bolus is larger than a fourth temporal distance between a) the first end of the single combination sub-bolus, which has the first labeling state, of the second combination bolus and b) the second end of the second combination bolus; and
   wherein the sub-bolus length determination unit is configured to determine the sub-bolus length of the fluid bolus, to which the further image corresponds, based on the first and second combination images.

4. The imaging system of claim 3 wherein the image acquisition unit is configured to acquire the series of images at the second location such that these images and also the first and second combination images show a tissue of interest, wherein the sub-bolus length determination unit is configured to:
   determine a first parameter, which is indicative of the amount of fluid, which has the first labeling state, in the tissue of interest shown in the first combination image, based on the first combination image and a second parameter, which is indicative of the amount of fluid, which has the first labeling state, in the tissue of interest shown in the second combination image, based on the second combination image; and determine the sub-bolus length based on the first and second parameters.

5. The imaging system of claim 4 wherein the tissue of interest is a capillary bed and the sub-bolus length determination unit is configured to determine the sub-bolus length such that:

it is smaller than the length of a first sub-bolus of the fluid bolus, to which the image of the series of images corresponds, which is acquired immediately before the further image is acquired, if the first parameter is larger than the second parameter, and/or it is larger than the length of a first sub-bolus of the fluid bolus, to which the image of the series of images corresponds, which is acquired immediately before the further image is acquired, if the first parameter is smaller than the second parameter.

6. The imaging system of claim 4 wherein the sub-bolus length determination unit is configured to determine the sub-bolus length depending on a ratio of the first and second parameters.

7. The imaging system of claim 6 wherein the tissue of interest is the capillary bed and the sub-bolus length determination unit is configured to determine the sub-bolus length such that:

it is smaller than the length of a first sub-bolus of the fluid bolus, to which the image of the series of images corresponds, which is acquired immediately before the further image is acquired, if the ratio is smaller than a predefined threshold, and/or it is larger than the length of a first sub-bolus of the fluid bolus, to which the image of the series of images corresponds, which is acquired immediately before the further image is acquired, if the ratio is larger than a predefined threshold.

8. The imaging system of claim 4 wherein the sub-bolus length determination unit is configured to determine the first parameter based on the number of image elements of the first combination image having an image value being larger than a threshold in the first combination image and to determine the second parameter based on the number of image elements of the second combination image having an image value being larger than a threshold in the second combination image.

9. The imaging system of claim 8 wherein the sub-bolus length determination unit is configured to generate a histogram of the image values in the respective combination image and determine a smallest maximum image value of the histogram as the threshold.

10. The imaging system of claim 1 wherein the bolus generating unit is configured to generate the further fluid bolus such that the first sub-bolus of this further fluid bolus has the determined sub-bolus length.

11. The imaging system of claim 10 wherein the fluid boli have a same temporal length, wherein the difference between the time of generating a respective fluid bolus and the acquisition time for acquiring the respective image is the same for all combinations of the respective image and a corresponding respective fluid bolus, wherein each sub-bolus has a first and a second end, wherein the first end is generated earlier than the second end, wherein the image acquisition unit is configured to acquire the series of images at the second location such that it shows a capillary bed, wherein the sub-bolus length determination unit, the bolus generation unit and the image acquisition unit are configured such that the time period between a) the time, at which the second end of the first sub-bolus of the further fluid bolus is generated at the first location, and b) the time, at which the further image which corresponds to the further fluid bolus is acquired at the second location, is equal to or larger than the time needed by the second end of the first sub-bolus to be flowed from the first location to the second location and into the capillary bed.

12. The imaging system of claim 11 wherein each fluid bolus has first and second ends, wherein the first end is generated earlier then the second end, wherein the bolus generation unit and the image acquisition unit are configured such that the time period between a) the time, at which the second end of the further fluid bolus is generated at the first location and b) the acquisition time of the further image at the second location is predetermined, wherein the bolus generating unit is configured to determine the further fluid bolus such that the temporal length of the further fluid bolus is predetermined, wherein the sub-bolus length determination unit is configured to determine the sub-bolus length of the first sub-bolus of the further fluid bolus such that the time period between a) the time, at which the second end of the first sub-bolus is generated, and b) the time, at which the further image which corresponds to the further fluid bolus comprising the first sub-bolus is acquired, is equal to or larger than the time needed by the second end of the first sub-bolus to be flowed from the first location to the second location and into the capillary bed.

13. The imaging system of claim 1 wherein the bolus generating unit is configured to generate the fluid boli, to which the images correspond, such that they are representable by a matrix, wherein each row of the matrix represents a respective fluid bolus, wherein a sub-bolus, which has a first labeling state, of a fluid bolus is represented by a) one or several matrix elements having a same matrix value indicating a first labeling state or b) a single matrix element indicating a first labeling state, wherein a sub-bolus, which has a second labeling state, of a fluid bolus is represented by a) one or several matrix elements having a same matrix value indicating a second labeling state or b) a single matrix element indicating a second labeling state.

14. The imaging system of claim 13 wherein the matrix is a Hadamard matrix or a matrix comprising rows of a Hadamard matrix and an inserted additional row, wherein the additional row is generated by using an existing row of the Hadamard matrix, wherein matrix values indicating the first labeling state are replaced by matrix values indicating the second labeling state and vice versa.

15. The imaging system of claim 14 wherein the Hadamard matrix is a non-mirrored Walsh-ordered Hadamard matrix or Walsh-ordered Hadamard matrix mirrored left to right.

16. An imaging method for generating a series of images of a subject, wherein the imaging method comprises:

generating fluid boli at a first location of the subject by a bolus generating unit, wherein each fluid bolus comprises a sequence of sub-boli, wherein each sub-bolus has one of at least two different labeling states;

acquiring images of the series of images at a second location of the subject by an image acquisition unit, after the fluid boli have been flowed from the first location to the second location, wherein each image corresponds to a respective fluid bolus;

determining a sub-bolus length based on at least one image of the acquired images of the series of images by a sub-bolus length determination unit;

generating a further fluid bolus comprising a further sequence of sub-boli at the first location by the bolus generating unit, wherein at least one of the sub-boli of the further sequence of sub-boli have the determined sub-bolus length; and acquiring a further image of the series of images at the second location of the subject by the image acquisition unit, after the further fluid bolus has been flowed from the first location to the second location.

17. A non-transitory computer readable memory medium containing computer program instructions for controlling a computer processor, when executed, to cause an imaging system to perform a method comprising:

generating fluid boli at a first location of the subject, wherein each fluid bolus comprises a sequence of sub-boli, wherein each sub-bolus has one of at least two different labeling states;

acquiring images of the series of images at a second location of the subject, after the fluid boli have been flowed from the first location to the second location, wherein each image corresponds to a respective fluid bolus;

determining a sub-bolus length based on at least one image of the acquired images of the series of images;

generating a further fluid bolus comprising a further sequence of sub-boli at the first location, wherein at least one of the sub-boli of the further sequence of sub-boli have the determined sub-bolus length; and acquiring a further image of the series of images at the second location of the subject, after the further fluid bolus has been flowed from the first location to the second location.

* * * * *